US006432961B1

(12) United States Patent
Uylenbroeck et al.

(10) Patent No.: US 6,432,961 B1
(45) Date of Patent: *Aug. 13, 2002

(54) METHOD FOR PREVENTING THE ONSET OF ASTHMA

(75) Inventors: Luc Uylenbroeck, Braine-l'Alleud; Marc De Longueville, Brussels; Anne Wilmes, La Hulpe; Johan De Clercq, Dilbeek, all of (BE)

(73) Assignee: UCB S.A., Brussels (BE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/375,414

(22) Filed: Aug. 17, 1999

Related U.S. Application Data

(60) Provisional application No. 60/096,929, filed on Aug. 18, 1998.

(51) Int. Cl.$^7$ .............................................. A61K 31/495
(52) U.S. Cl. ................................................ 514/255.04
(58) Field of Search ............................ 514/255, 255.04

(56) References Cited

U.S. PATENT DOCUMENTS

| 4,525,358 A | 6/1985 | Baltes et al. ................. 514/255 |
| 5,478,941 A | 12/1995 | Cossement et al. .......... 544/383 |
| 5,698,558 A | 12/1997 | Gray .......................... 514/255 |

FOREIGN PATENT DOCUMENTS

| EP | 0 058 146 | 8/1982 |
| EP | 0 617 028 | 9/1994 |
| EP | 0 661 975 | 3/1999 |
| GB | 2 311 940 | 1/1997 |
| WO | 94/06429 | 3/1994 |
| WO | 94/06430 | 3/1994 |

OTHER PUBLICATIONS

K. P. Paul, "ETAC: an Update", International Journal of Immunopathology and Pharmacology, vol. 10, No. 2, pp. 127–128, 1997.
U. Waln, "Allergic factors associated with the development of asthma and the influence of cetirizine in a double-blind, randomised, placebo-controlled trial: First results of ETAC", Pediatric Allergy and Immunology, vol. 9, No. 3, pp. 116–124, Aug. 1998.
L. Fasce et al., "Cetirizine Reduces ICAM–I on Epithelial Cells during Nasal Minimal Persistent Inflammation in Asymptomatic Children with Mite–Allergic Asthma", Int. Arch. Allergy Immunol. vol. 109, No. 3, pp. 272–276, 1996.
A. Brik et al., "Effect of cetirizine, a new histamine $H_1$ antagonist, on airway dynamics and responsiveness to inhaled histamine in mild asthma", vol. 80, No. 1, pp. 51–56, 1987.
J.O. Warner et al, "Determinants of total and specific IgE in infants with atopic dermatitis", Pediatric Allergy and Immunology, vol. 8, pp. 177–184, Nov. 1997.

J.H. Dijkman et al., "Prophylactic treatment of grass pollen–induced asthma with cetirizine", Clinical and Experimental Allergy, vol. 20, pp. 483–490, Sep. 1990.
C. De Vos et al., "Antihistamines and allergic asthma", Allergie et Immunologie, vol. 23, No. 9, pp. 396–401, Nov. 1991.
D. Tashkin et al., "Cetirizine inhibition of histamine–induced bronchospasm", vol. 59, pp. 49–52, Dec. 1987.
G. Bruttmann et al., "Protective effect of cetirizine in patients suffering from pollen asthma", Annals of Allergy, vol. 64, pp. 224–228, Feb. 1990.
H. Redier et al., "Inhibitory effect of cetirizine on the bronchial eosinophil recruitment induced by allergen inhalation challenge in allergic patients with asthma", Journal of Allergy and Clinical Immunology, vol. 90, No. 2, pp. 215–224, Aug. 1992.
J.B. Wasserfallen et al., "Effect of cetirizine, a new $H_1$ antihistamine, on the early and late allergic reactions in a bronchial provocation test with allergen", Journal of Allergy and Clinical Immunology, vol. 91, No. 6, pp. 1189–1197, Jun. 1993.
J.A. Grant et al., "Safety and efficacy of cetirizine (CET) in the prophylactic management of patients with seasonal allergic rhinitis (SAR) and asthma", vol. 91, No. 1, p. 197, Mar. 12–17, 1993.
"Medical researchers aim at fundamental better protection and treatment of the atopic child", ETAC Science, pp. 1–8, Jan. 1994.
Trieloff, I., Pädiatrie, "Asthma prevention in risk children: Cetirizine", pp. 61–62, 1995.
Allergo, "Early treatment of the atopic child", pp. 390–391, 1995.
Castello, D., Riv. Ital. Pediatr., "The role of early intervention in childhood asthma therapy", pp. 8224–827, 1998.
E. Bidat et al., Le Concours Médical, "The treatment of childhood asthma", pp. 3021–3026, 1991.
L. Businco et al., Minerva Pediatrica, "From atopic dermatitis to asthma", pp. 477–481, 1997.
B. Schwarz, Pharmazie, "Treatment with cetirizine also for children", p 34, 1993.
S. Matsubara et al., Japanese Pharmacology & Therapeutics, 25(4) "Effect of betotastine basilate on experimental asthma model in guinea pigs", pp. 31–36, 1997.
J.O. Warner, "Early treatment of the atopic child", Pediatric Allergy and Immunology, vol. 8, (Suppl. 10, pp. 46–48, 1997.
Schwartz, "Cetirizin auch fur kleine kinder", Pharmazie, vol. 20, No. 138, p. 34, May 20, 1993, with English translation.
ANONYM, "Mit ETAC gegen fruhes allergisches asthma", Notfall Medizin, vol. 21, No. 3, p. 157, 1995, with English translation.

*Primary Examiner*—Phyllis G. Spivack
(74) *Attorney, Agent, or Firm*—Wenderoth, Lind & Ponack, L.L.P.

(57) ABSTRACT

The present invention relates to a method for preventing the onset of asthma which comprises administering to a patient a therapeutically effective amount of cetirizine, an individual optical isomer thereof or a pharmaceutically acceptable salt thereof.

21 Claims, 2 Drawing Sheets

METHOD FOR PREVENTING THE ONSET OF ASTHMA

Figure 1:
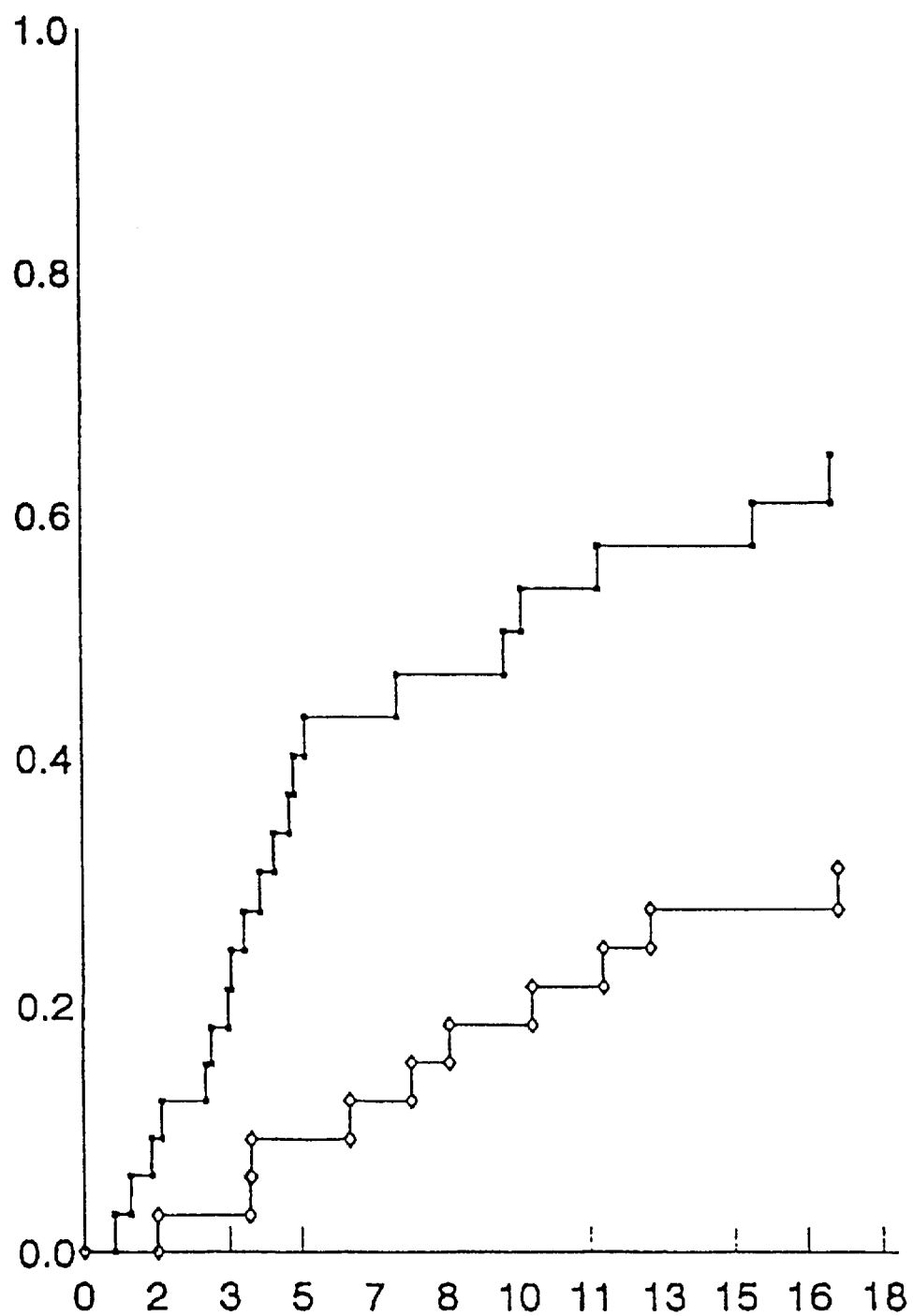

This application claims the benefit of U.S. provisional application No. 60/096,929, filed on Aug. 18, 1998.

The present invention relates to a method for preventing the onset of asthma with cetirizine, an individual optical isomer thereof or a pharmaceutically acceptable salt thereof.

The prevalence of asthma, atopic dermatitis and hay fever has increased over the last three decades in many countries (ISAAC, Lancet 1998: 351: 1225–32) and the health and economic burden of these diseases are considerable. So far, no intervention has been shown to alter the natural history of asthma and hay fever. It is known that exposure to high levels of allergen in early life is a major trigger for asthma (U. WAHN et al., Pediatr. Allergy Immunol. 1997:8 (10 suppl): 16–20). Attempts at prevention of allergen avoidance have produced conflicting results with no benefit at all (R. S. ZEIGER et al., Pediatr. Allergy Immunol. 1992: 3: 110–27), only transient effects or, in the case of one study, a long lasting effect (U. M. SAARINEN et al., Lancet 1995: 346: 1065–69; D. W. HIDE et al., Allergy: 51(2): 89–93). There is also a strong association between atopic dermatitis and the subsequent development of asthma. Around 40% of infants with atopic dermatitis in early infancy will develop asthma at the age of 3 to 4 years.

Clearly, the prevalence of asthma and its consequences call for effective methods of preventing asthma.

There are two studies reporting the prophylactic use of ketotifen for the prevention of asthma in preasthmatic children with non specific elevated IgE level (Y. likura et al., Ann. Allergy 1992: 68: 233–36; G. J. BUSTOS et al., Clin. Exp. Allergy 1995: 25(6): 568–73). However, the use of ketotifen in infants and very young children is often associated with side-effects such as drowsiness or nervous excitation.

Therefore, it remains desirable to find other therapeutic methods and pharmaceutical compositions for preventing the onset of asthma, in particular in infants or young children.

The first purpose of the invention concerns the primary prevention of asthma prevention of sensitisation of infants at risk of developing asthma diseases.

The second purpose of the invention is the prevention of allergic asthma in infants at high risk and evidence of aeroallergen (grass pollen or house dust mite) sensitization.

The present invention is based on the unexpected recognition that administration of pharmaceutical compositions comprising cetirizine, an individual optical isomer thereof or a pharmaceutically acceptable salt thereof to infants prevents the onset of asthma.

The present invention encompasses a method for preventing or retarding the onset of asthma which comprises administering to a patient a therapeutically effective amount of cetirizine, an individual optical isomer thereof or a pharmaceutically acceptable salt thereof.

The present invention also encompasses the use of cetirizine, an individual optical isomer thereof or a pharmaceutically acceptable salt thereof for the preparation of a medicament intended for the prevention of asthma.

The present invention also concerns the use of cetirizine intended for preventing the onset of asthma in a patient, the said medicament being administered to the patient to the patient prior the onset of asthma (e.g. before any biological or clinical symptoms of allergic disease occurs (primary prevention) or after biological signs of sensitization to allergens but before the onset of symptoms of asthma (secondary prevention)).

The present invention also concerns the use of cetirizine, an individual optical isomer thereof or a pharmaceutically acceptable salt thereof for the preparation of a medicament intended for preventing the onset of asthma in a patient, the said medicament being administered to the patient prophylactically prior to the onset of asthma.

The present invention also concerns the use of cetirizine, an individual optical isomer thereof or a pharmaceutically acceptable salt thereof for the preparation of a medicament intended for preventing the sensitisation of patient at risk of developing asthma diseases.

The term cetirizine as used herein refers to 2-[2-[4-(4-chlorophenyl)phenylmethyl]-1-piperazinyl]ethoxy]acetic acid. Processes for preparing cetirizine, an individual optical isomer thereof or a pharmaceutically acceptable salt thereof have been described in European Patent 0 058 146, Great Britain Patent 2.225.320, Great Britain Patent 2.225.321, U.S. Pat. No. 5,478,941, European Patent application 0 601 028, European Patent Application 0 801 064 and International Patent Application WO 97/37.982.

The term "pharmaceutically acceptable salts" as used herein refers not only to addition salts with pharmaceutically acceptable non-toxic organic and inorganic acids, such as acetic, citric, maleic, succinic, ascorbic, hydrochloric, hydrobromic, sulfuric, and phosphoric acids and the like, but also its metal salts (for example sodium or potassium salts) or ammonium salts, the amine salts and the aminoacid salts. The best results have been obtained with cetirizine dihydrochloride.

The term "individual optical isomer" as used herein means the levorotatory and the dextrorotatary enantiomers of cetirizine. More precisely, it means that the active substance comprises at least 90% by weight, preferably at least 95% by weight, of one individual optical isomer of cetirizine and at most 10% by weight, preferably at most 5% by weight, of the other individual optical isomer of cetirizine. Each individual optical isomer may be obtained by conventional means, i.e., resolution from the corresponding racemic mixture or by asymmetric synthesis.

By patient, we understand infants and children, in particular young children. Generally, the patients are infants or children aged 3 months to 10 years, preferably aged 6 months to 5 years, and more preferably 10 months to 5 years. The best results have been obtained with patients aged 1 to 4 years.

According to the invention, the patient is not affected by asthma disease. Preferably, the patient has never been affected by asthma diseases.

Asthma is an inflammatory disease. Symptoms are presence of cough and/or wheezing, in particular recurrent cough and/or wheezing, and more specifically allergic wheezing or nocturnal cough with sleep disturbance lasting for at least 2 consecutive nights. Asthma can be defined as at least 2 separate episodes of nocturnal cough with sleep disturbances lasting for 2 consecutive nights or 2 separate episodes of wheezing. Asthma attack is defined as any episode of nocturnal cough with sleep disturbances lasting for 2 consecutive nights or any episode of wheezing requiring treatment; the second episode of wheezing or nocturnal cough is to be considered as the first asthma attack.

A therapeutically effective amount of cetirizine, an individual optical isomer thereof or a pharmaceutically acceptable salt thereof is used to alleviate the effects of an asthma attack or to prevent or retard onset of an asthma attack. The dosage depends essentially on the specific method of administration and on the purpose of the prophylaxis. The size of the individual doses and the administration program can best be determined based on an individual assessment of the relevant case. The methods required to determine the relevant factors are familiar to the expert.

A preferred daily dosage provides from about 0.0005 mg to about 2 mg of cetirizine, an individual optical isomer thereof or a pharmaceutically acceptable salt thereof, per kg of body weight per patient. A particularly preferred daily dosage is from about 0.005 to about 2 mg per kg of body weight per patient. The best results have been obtained with a daily dosage from about 0.05 to 1 mg per kg of body weight per patient. The dosage may be administered once per day of treatment, or divided into smaller dosages, for examples 1 to 4 times a day, and preferably 1 to 3 times a day, and administrated over about a 24 hours time period to reach a total given dosage. Best results have been obtained with an administration twice a day; the pharmaceutical compositions of the invention are taken in two equal doses per day. The exact dosages in which the compositions are administrated can vary according to the type of use, the mode of use, the requirements of the patient, as determined by a skilled practitioner. The exact dosage for a patient may be specifically adapted by a skilled person in view of the severity of the condition, the specific formulation used, and other drugs which may be involved.

Pharmaceutical compositions used according to the present invention may be administered by any conventional means. The routes of administration include intradermal, transdermal, slow release administration, intramuscular, oral and intranasal routes. Any other convenient route of administration can be used, for example absorption through epithelial or mucocutaneous linings.

The pharmaceutical forms according to the present invention may be prepared according to conventional methods used by pharmacists. The forms can be administered together with other components or biologicaly active agents, pharmaceutically acceptable surfactants, excipients, carriers, diluents and vehicles.

The pharmaceutical compositions of the invention include any conventional therapeutical inert carrier. The pharmaceutical compositions can contain inert as well as pharmacodynamically active additives. Liquid compositions can for example take the form of a sterile solution which is miscible with water. Furthermore, substances conventionally used as preserving, stabilizing, moisture-retaining, and emulsifying agents as well as substances such as salts for varying the osmotic pressure, substances for varying pH such as buffers, and other additives can also be present. If desired an antioxidant can be included in the pharmaceutical compositions. Pharmaceutical acceptable excipients or carriers for compositions include saline, buffered saline, dextrose or water. Compositions may also comprise specific stabilizing agents such as sugars, including mannose and mannitol. Carrier substances and diluents can be organic or inorganic substances, for example water, gelatine, lactose, starch, magnesium stearate, talc, gum arabic, polyalkylene glycol and the like. A prerequisite is that all adjuvants and substances used in the manufacture of the pharmaceutical compositions are nontoxic.

Pharmaceutical compositions can be administered by spray inhalation. Any conventional pharmaceutical composition for spray inhalation administration may be used. Another preferred mode of administration is by aerosol.

The pharmaceutical composition of the invention can also be formulated for topical application. The composition for topical application can be in the form of an aqueous solution, lotion or jelly, an oily solution or suspension or a fatty or emulsion ointment.

The pharmaceutical composition of the invention can also be used for slow prolonged release with a transdermal therapeutic system in polymer matrix or with an appropriate formulation for oral slow release.

The pharmaceutical compositions according to the present invention may also be administered orally or rectally. They may also be administered by nasal instillation (aerosols) or in the form of unguents or creams. The pharmaceutical compositions which can be used for oral administration may be solid or liquid, for example, in the form of uncoated or coated tablets, pills, dragees, gelatine capsules, solutions, syrups and the like. For administration by the rectal route, the compositions containing the compounds of the present invention are generally used in the form of suppositories.

The pharmaceutical forms, such as tablets, drops, suppositories and the like, are prepared by conventional pharmaceutical methods. The compounds of the present invention are mixed with a solid or liquid, non-toxic and pharmaceutically acceptable carrier and possibly also mixed with a dispersing agent, a disintegration agent, a stabilizing agent and the like. If appropriate, it is also possible to add preservations, sweeteners, coloring agents and the like.

Preferably, the pharmaceutical compositions of the invention is administered in traditional form for oral administration, as film coated tablets, lozenges, dragees, and oral liquid preparation such as syrup.

Best results have been obtained with an oral dosage form, in particular liquid formulations such as syrup. For example, patients can receive 2 doses of 0.25 mg/kg (total daily dose: 0.50 mg/kg/day) of an oral solution of cetirizine 10 mg/ml per day; one ml of the solution contains 20 drops and one drop of cetirizine solution contains 0.5 mg.

As an Example of a composition according to the present invention, the following formulation of a syrup is preferred: cetirizine dihydrochloride, methyl- and propylparaben, saccharinum,and purified water.

As an Example of a composition according to the present invention, the following formulation of a film coated tablet is preferred: cetirizine dihydrochloride, magnesium stearate, cellulose, lactose and silicon dioxide.

Pharmaceutical compositions of the invention are useful prophylactically. These compositions can alleviate the effects of the asthma attack. These compositions can delay or prevent onset of asthma.

Pharmaceutical compositions of the invention allow to decrease the need of corticoid compounds, such as corticosteroids, needed for any allergic disease.

Another advantage of the invention is the ability of the process to prevent onset of asthmatic attacks and to reduce symptoms subsequent to its initiation. The method of the invention is believed particularly suited to use in patients susceptible to pulmonary inflammation.

Another advantage of the invention takes place in the fact that an early treatment with cetirizine dihydrochloride (initiated between 1 and 2 years of age) halved the number of children developing asthma, when they were suffering from atopic dermatitis and were sensitized (raised specific IgE antibody levels $\geq 0.35$ kUA/l) to grass pollen or house dust mite.

The invention allow to decrease the relative risk for developing asthma, in children sensitized to egg, milk, cat, house dust mite and grass pollen.

The pharmaceutical composition of the invention is used to prevent the onset of asthma in patients considered to be at high risk of developing the disease. These patients have been described as preasthmatic but are still asthma free.

Figure 2:
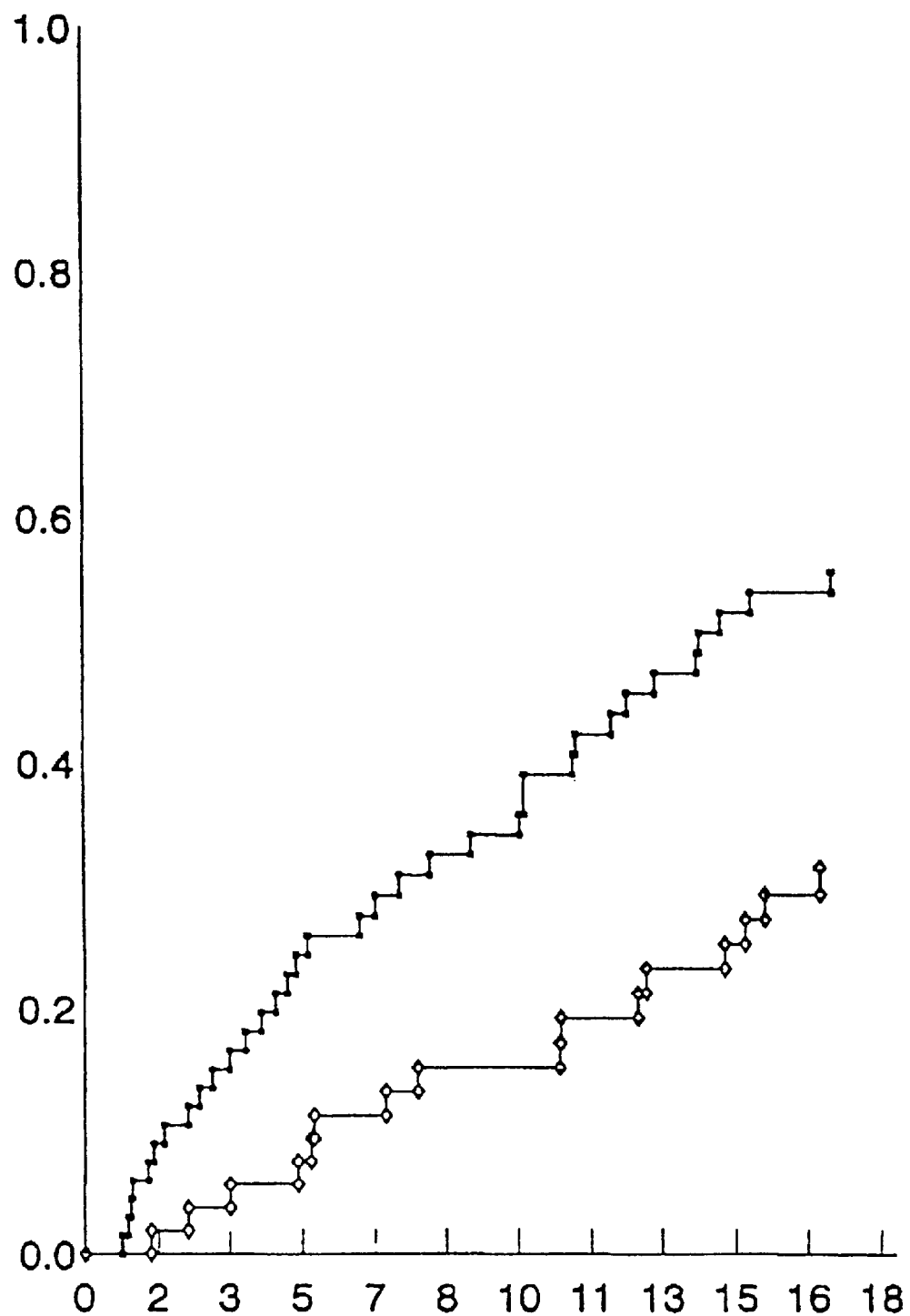

FIG. 1 and 2 represent the occurrence of asthma by treatment in patients sensitised respectively to house dust mite at baseline for FIG. 1 (Cetirizine (N=36) and Placebo (N=34)) and to grass pollen at baseline for FIG. 2 (Cetirizine (N=56) and Placebo (N=68)). The abscissa represents the time (months) and the ordinate represents the probability for developing asthma. The curve with -.- corresponds to the placebo, and the curve with -♦- corresponds to cetirizine dihydrochloride treatment.

The invention is further defined by reference to the following example.

EXAMPLE

The aim of the study relative to the clinical effect of cetirizine dihydrochloride was to establish on the intention to treat (ITT population) whether an 18 month cetirizine dihydrochloride treatment can prevent the onset of asthma in young children with atopic dermatitis, when compared to placebo. Subgroups based on the baseline status of biological markers as well as specific asthmatic patients (i.e. wheezers only; asthma onset date at least 3 months after inclusion) were foreseen as well. It was considered that a 30% reduction of the incidence of asthma is clinically relevant. Secondary parameters of efficacy included the severity of asthma and atopic dermatitis. The safety of this long-term treatment with cetirizine dihydrochloride in infants has also been evaluated.

The target population of this example consisted of infants aged 1 to 2 years with active symptoms of atopic dermatitis for at least one month before enrollment. All the infants had to have at least one parent or sibling with a history of atopic disease (atopic dermatitis, allergic rhinitis or asthma). Excluded were infants with asthma, or with a history of any episodes of wheezing or nocturnal cough as well as any condition likely to obscure the diagnosis of asthma (Guidelines for the diagnosis and management of asthma. National Asthma Education and Prevention Program. Expert Panel Report II. National Institute of Health publication 97-4051; International Report. International consensus report on diagnosis and treatment of asthma. National Heart, Lung and Blood Institute. National Institute of Health publication 92-3091).

The study was a prospective, randomized, double blind, parallel group, and placebo-controlled study with cetirizine dihydrochloride.

The severity of atopic dermatitis was rated with the atopic dermatitis scale SCORAD (Consensus Report of the European Task Force on Atopic Dermatitis. Severity Scoring of Atopic Dermatitis: the SCORAD Index. Dermatology 1993; 186: 23–31.).

Study treatment lasted for 18 months. After the treatment period, patients entered a long-term follow-up period.

The primary end-point for efficacy was the onset of asthma, defined as 3 episodes of nocturnal cough with sleep disturbances or wheezing, separated by at least 7 days, in a clinical setting where asthma is likely and conditions other than allergy have been excluded.

Secondary parameters of efficacy included the severity of asthma, consumption of concomitant medications and the severity of symptoms related to the atopic dermatitis evaluated according to the SCORAD score.

Serum total and specific (grass pollen, cow's milk, egg, house dust mites and cat dander) IgE antibody levels were determined using the Pharmacia CAP® system (Pharmacia & Upjohn, Uppsala, Sweden). These analyses were made at baseline, and after 3, 12 and 18 months of treatment by a central laboratory (Institut Pasteur—Lille, France) according to instructions of the manufacturer and routine clinical laboratory performances.

At each of the nine visits, the atopy status, any concurrent illnesses, concomitant medications and procedures were recorded. Patients underwent a physical examination, including the measurement of vital signs.

Adverse events were recorded by the parents on diary cards and discussed with the investigator at each visit. Serious adverse events had to be reported immediately.

Oral solutions of cetirizine dihydrochloride (10 mg/ml) and matching placebo, similar in appearance and taste were used. The recommended study dosage was 0.25 mg cetirizine/kg b.i.d. (b.i.d.="bis in die", 2 times a day).

Sample size was based on an expected cumulative incidence of asthma in 40% of children in the placebo group after 18 months of treatment. A decrease of 30% of the incidence was considered as clinically relevant.

The baseline characteristics of the two treatment groups, including the mean SCORAD values, family history of atopy and environmental factors were comparable.

Infants in the placebo group, with raised baseline levels of serum total IgE ($\geq$30 kU/l) or specific IgE antibodies ($\geq$0.35 kUA/l) had an increased relative risk of developing asthma (Table 1). This increase was observed for all measured IgE antibodies and was significant for total IgE, grass pollen, house dust mite and cat dander allergens.

The present study is the first to show that sensitization to grass pollen in such young infants is a powerful predictor of future onset of asthma.

Analysis of the subgroups based on immunological parameters showed statistically significant differences of high clinical relevance. (Table 2—FIGS. 1 and 2).

Infants receiving cetirizine dihydrochloride, who began the study with raised baseline levels of total IgE ($\geq$30 kU/l) or specific IgE antibodies ($\geq$0.35 kUA/l) had a reduced risk of developing asthma compared with those infants with raised baseline IgE antibodies, who received placebo.

This reduction was observed for all measured IgE antibodies and was significant for grass pollen (p=0.002) and house dust mite (p=0.005), either alone or combined (FIGS. 1 and 2).

There were no significant differences in the adverse event (AE) profiles between groups except for urticaria (16.1% versus 5.8%, p<0.001) which was less frequent in the cetirizine group.

The study shows that early treatment with cetirizine dihydrochloride (initiated between 1 and 2 years of age) halved the number of children developing asthma, when they were suffering from atopic dermatitis and were sensitized (raised specific IgE antibody levels $\geq$0.35 kUA/l) to grass pollen or house dust mite.

Inclusion criteria were pragmatic and based on simple clinical assessment: atopic dermatitis was defined using well-published standard criteria (T. L. DIEPGEN et al., J Clin Epidemiol 1996; 49(9): 1031–38.; H. A. SAMPSON, Ann Allergy 1992; 69(6): 469–79.).

Cetirizine dihydrochloride significantly reduced the risk of subsequent asthma in infants with the strongest predictors for developing it. For these infants who were sensitized to grass pollen or house dust mite, the relative risk of subsequent asthma was reduced to 0.5 and 0.6 respectively.

While it is clear that antihistamines do not play a major role in the treatment of asthma, cetirizine has the potential to prevent the onset of asthma. This hypothesis is substantiated by the present findings. Allergic asthma has been prevented in infants at high risk and evidence of aeroallergen (grass pollen or house dust mite) sensitization. As early house dust mite sensitivity in childhood asthma is associated with persistent symptoms in long-term follow-up (R. SPORIK et al., N Eng J Med 1990; 323(8): 502–07.), it is likely that this intervention will be highly cost-effective.

This large trial in infants has shown that cetirizine dihydrochloride is a safe product. This double-blind trial of the use of cetirizine dihydrochloride in infants with atopic dermatitis shows that it successfully prevents asthma in infants with evidence of sensitivity to either grass pollen or house dust mite.

TABLE 1

Occurrence of Asthma by Baseline Atopic Characteristics Placebo ITT Population (n = 397)

|  | Normal (%) | Elevated (%) | RR for developing asthma in presence of elevated marker [95% CI] | Log-Rank Test p value |
|---|---|---|---|---|
| Total IgE (PRIST)* | (33.5) | (43.6) | 1.3 [1.0;1.7] | 0.027 |
| IgE Grass pollen (GX1)* | (35.0) | (58.8) | 1.7 [1.2;2.3] | <0.001 |
| IgE HDM (D1)* | (34.7) | (51.5) | 1.5 [1.1;2.0] | 0.005 |
| IgE Cat dander (E1)* | (33.2) | (47.1) | 1.4 [1.0;1.9] | 0.032 |
| IgE Egg (F1)* | (30.7) | (39.3) | 1.3 [0.9;1.8] | 0.152 |
| IgE Milk (F2)* | (36.0) | (40.9) | 1.1 [0.9;1.5] | 0.250 |
| IgE HDM + Grass Pollen | (32.9) | (53.7) | 1.6 [1.2;2.1] | <0.001 |
| Eosinophil count | (34.9) | (47.6) | 1.4 [1.0;1.9] | 0.066 |

ITT Intention-to-treat
RR relative risk
CI confidence interval
( )*Pharmacia & Upjohn Diagnostics references
HDM House Dust Mite
Elevated values Total IgE:≧30 kU/l,
Specific IgE:≧0.35 kUA/l,
Eosinophils:>0.7 giga/l

TABLE 2

Occurrence of Asthma by Treatment in the ITT population

|  | Placebo (%) | Cetirizine (%) | RR for developing asthma when cetirizine treated [95% CI] | Log-Rank Test p value |
|---|---|---|---|---|
| ITT population | (38.0) | (37.7) | [0.8;1.2] | 0.973 |
| Subgroups with elevated IgE or eosinophils at baseline | | | | |
| Total IgE (PRIST)* | (43.6) | (38.1) | 0.9 [0.7;1.1] | 0.391 |
| IgE Grass pollen (GX1)* | (58.8) | (27.8) | 0.5 [0.3;0.9] | 0.002 |
| IgE HDM (D1)* | (51.5) | (28.6) | 0.6 [0.3;0.9] | 0.005 |
| IgE Cat dander (E1)* | (47.1) | (40.6) | 0.9 [0.6;1.3] | 0.610 |
| IgE Egg (F1)* | (39.3) | (31.2) | 0.8 [0.6;1.1] | 0.292 |
| IgE Milk (F2)* | (40.9) | (30.7) | 0.7 [0.5;1.0] | 0.140 |
| IgE HDM + | (53.7) | (34.2) | 0.6 | 0.006 |

TABLE 2-continued

Occurrence of Asthma by Treatment in the ITT population

|  | Placebo (%) | Cetirizine (%) | RR for developing asthma when cetirizine treated [95% CI] | Log-Rank Test p value |
|---|---|---|---|---|
| Grass pollen Eosinophil count | (47.6) | (42.7) | [0.4;0.9] 0.9 [0.6;1.3] | 0.674 |

ITT Intention-to-treat
RR relative risk
CI confidence interval
( )*Pharmacia & Upjohn Diagnostics references
HDM House Dust Mite
Elevated values Total IgE:≧30 kU/l,
Specific IgE:≧0.35 kUA/l,
Eosinophils:>20.7 giga/l

What is claimed is:

1. A method for preventing or retarding the onset of asthma in a patient who has developed a sensitization to allergens but who has no personal history of asthma, said patient having a total IgE level of greater or equal to 30 kU/l or a specific IgE antibody level of greater or equal to 0.35 kUA/l, which comprises administering to said patient a therapeutically effective amount of a pharmaceutical composition comprising cetirizine, an individual optical isomer thereof, or a pharmaceutically acceptable salt thereof.

2. The method of claim 1, wherein said salt is cetirizine dihydrochloride.

3. The method of claim 1, wherein said patient is an infant or a child.

4. The method of claim 1, wherein said patient is aged 1 to 4 years.

5. The method of claim 1, wherein said patient is administered a daily dosage of from about 0.0005 mg to about 2 mg of said cetirizine, said individual optical isomer thereof, or said pharmaceutically acceptable salt thereof, per kg of body weight of said patient.

6. The method of claim 5, wherein said patient is administered a daily dosage of from about 0.05 mg to about 1 mg, per kg of body weight of said patient.

7. The method of claim 1, wherein said composition is administered 1 to 3 times a day.

8. The method of claim 1, wherein said composition is administered orally.

9. The method of claim 1, wherein said asthma is allergic asthma disease caused by sensitization of said patient to an allergen.

10. The method of claim 1, wherein the patient is a child between the ages of 3 months and 10 years of age.

11. The method of claim 1, wherein the patient has developed atopic dermatitis.

12. A method for preventing the sensitization of a patient to allergens, said patient being at risk of developing an asthma disease but having no personal history of asthma, and said patient having a total IgE level greater or equal to 30 kU/l or a specific IgE antibody level of greater or equal to 0.35 kUA/l, which comprises administering to said patient a therapeutically effective amount of pharmaceutical composition comprising cetirizine, an individual optical isomer thereof, or a pharmaceutically acceptable salt thereof.

13. The method of claim 12, wherein said salt is cetirizine dihydrochloride.

14. The method of claim 12, wherein said patient is an infant or a child.

15. The method of claim 12, wherein said patient is aged 1 to 4 years.

16. The method of claim 12, wherein said patient is administered a daily dosage of from about 0.0005 mg to about 2 mg of said cetirizine, said individual optical isomer thereof, or said pharmaceutically acceptable salt thereof per kg of body weight of said patient.

17. The method of claim 16, wherein said patient is administered a daily dosage of from about 0.05 mg to about 1 mg, per kg of body weight of said patient.

18. The method of claim 12, wherein said composition is administered 1 to 3 times a day.

19. The method of claim 12, wherein said composition is administered orally.

20. The method of claim 12, wherein the patient is a child between the ages of 3 months and 10 years of age.

21. The method of claim 12, wherein the patient has developed atopic dermatitis.

* * * * *